United States Patent [19]
Bongen et al.

[11] Patent Number: 6,156,214
[45] Date of Patent: Dec. 5, 2000

[54] PROCESS FOR REMOVING MERCURY FROM ALKALI METAL ALKOXIDE SOLUTIONS

[75] Inventors: Marcus Bongen, Bonn; Marcel Feld, Cologne; Guenter Zoche, Bonn, all of Germany

[73] Assignee: Huels Aktiengesellschaft, Marl, Germany

[21] Appl. No.: 09/021,170

[22] Filed: Feb. 10, 1998

[30] Foreign Application Priority Data

Feb. 10, 1997 [DE] Germany .................... 197 04 889

[51] Int. Cl.⁷ .................... C02F 1/42; C22B 43/00
[52] U.S. Cl. .................... 210/914; 75/742; 75/724; 210/679; 210/688
[58] Field of Search .................... 75/724, 742; 210/679, 210/688, 914

[56] References Cited

U.S. PATENT DOCUMENTS 5,391,217  2/1995  Zoche .................... 75/724

FOREIGN PATENT DOCUMENTS 0 761 830    8/1996   European Pat. Off. .
0 761 830 A2 3/1997   European Pat. Off. .
2643478      4/1977   Germany .
55-048133    12/1980  Japan .

OTHER PUBLICATIONS

Pitlik, Harris A., "Looking Beyond Blazemarks on Trees—It's TIme to Revisit the Description Requirement in the Wake of Warner–Jenkinson", JPTOS, vol. 79, No. 9, pp. 625–642, Sep. 1997.

"Standardization of methods for the determination of traces of mercury Part 4. Determination of total mercury in gases by atomic absorption spectrometry", Anal. Chim. Acta, vol. 108: 1–11 (abstract only), 1979.

Duerr et al., "Determination of mercury and mercury compounds in air and other non–corrosive gases", Fresenius'Z. Anal. Chem., vol. 283(5), pp. 337–341 (abstract only), 1977.

*Primary Examiner*—Howard C. Lee
*Attorney, Agent, or Firm*—Oblon, Spivak, McClelland, Maier & Neustadt, P.C.

[57] ABSTRACT

A three-stage process for removing mercury contaminants from alcoholic alkali metal alkoxide solutions is provided, in which mercury is depleted in a first filtration through inert fibrous material, followed by a second filtration through pulverized coal, and then by concentration by distillation, to preferably provide a mercury content below 0.1 ppm.

18 Claims, No Drawings

PROCESS FOR REMOVING MERCURY FROM ALKALI METAL ALKOXIDE SOLUTIONS

BACKGROUND OF THE INVENTION

1. Field of the Invention

The present invention relates to a process for removing mercury contaminants from alcoholic alkali metal alkoxide solutions.

2. Discussion of the Background

The alkali metal alkoxides produced by the alkali metal amalgam process generally have an unwanted content of mercury in the ppm range. Mercury contents of 5 to 50 ppm can sometimes occur. In addition, based on analysis of these products, one reaches the conclusion that at least the majority of the mercury is present not in ionic form, but in zero-valent form ($Hg°$).

To increase product quality and to expand the area of use of these alkoxides, it is desirable to remove mercury residue from the solutions by means of a simple and, at the same time, economical process.

One possible method for removal of mercury is provided by the known property of mercury of forming amalgams. A suitable material for this is a fine-grained material charged with a silver layer or a suitable metal having a very high surface area, such as a wool, which may be used as an electrode in an electrolysis cell. Separating off mercury by amalgam formation is performed in DE-A42 21 207 using a silver-coated fiber and in DE-A-25 18 433 using nickel wool. However, media of these types are very rapidly exhausted if the mercury content of the solution is substantial, particularly when the volume of material processed is high over a relatively long period of time. They are thus comparatively uneconomical in such cases, since recovery of the expensive amalgam-forming metals is not always technically possible.

The removal of mercury from solution by treatment with activated carbon has also been disclosed. In DE-A-34 38 098, an activated carbon pretreated with mercury or with mercury salts is used in a filter bed. According to DE-A-26 43 478, activated carbon having a high specific surface area is suitable for removal of mercury, with no statement being made regarding the particle size of the activated carbon. An activated carbon treatment is described in DE-A-20 51 725 for the brines produced in chlor-alkali electrolysis.

Cleaning of mercury-contaminated waste waters is also disclosed in JP 831128 182. In this case, use is made of a tube which is provided at both the top and bottom with an acid-resistant resin filter and which contains, between the filters, 85 to 95% by volume of activated carbon and, above this, 15 to 5% by volume of coal dust. The activated carbon in this case has particle sizes of 50% above 20 mesh and 50% below 20 mesh, while the coal dust has particle sizes of about 60 mesh (20 mesh is equivalent to approximately 840 $\mu$m and 60 mesh to approximately 250 $\mu$m). The contaminated waste water is passed through the tube from top to bottom, with the coal dust removing the suspended matter and the activated carbon removing the harmful substances (especially mercury). Mercury contents are reduced from 37 mg/l to 0.0005 mg/l, for example, in this process.

A shared feature of the abovementioned processes is that they are designed to remove mercury from aqueous solutions. This can be taken from the examples. Their subject-matter is, in particular, the treatment of sodium hydroxide solution, soda solutions or brines. A simple conversion to alkali metal alkoxide solutions does not prove to be possible, due in part to a lack of efficiency, due in part to insufficient service lives, and due in part to the use of non-resistant filter aids.

Even the pulverized coal prefiltration of JP 83/128 182 is not applicable to alkali metal alkoxide solutions. Pulverized coals of this type are not able to retain the fine slurry-like impurities which are present in alkali metal alkoxide solutions from chlor-alkali electrolysis. A further disadvantage in the use of an extremely fine pulverized coal is that even small amounts of suspended matter, which may be present in the alkoxide solutions to be treated, can considerably decrease the service lives due to blockage.

To remove the suspended matter and slurries, centrifuges or separators are frequently used in industry. However, equipment of this type, because of moving parts, is susceptible to breakdown and requires intensive maintenance. A method which enables suspended matter to be removed in a simpler manner is therefore wanted.

SUMMARY OF THE INVENTION

Accordingly, one object of the present invention is to provide a process that enables mercury to be removed from alkali metal alkoxide solutions with high efficiency, preferably with a final concentration of less than 0.1 ppm of mercury.

A further object of the present invention is to provide a process for removal of mercury from alkali metal alkoxide solutions that is technically simple to perform and uses technically simple process means.

A further object of the present invention is to provide a process for removing mercury from alkali metal alkoxide solutions that can be performed with an economical service life for the equipment used.

These and other objects of the present invention have been satisfied by the discovery of a process for removing mercury contaminants from alcoholic alkali metal alkoxide solutions, which comprises a first filtration through inert fibrous material, a second filtration using a pulverized coal as filter aid, and then concentrating the alkali metal alkoxide solution by distillation.

DETAILED DESCRIPTION OF THE PREFERRED EMBODIMENTS

The present invention relates to a process for removing mercury metal and compounds from alcoholic alkali metal alkoxide solutions comprising a first filtration step of filtering the alcoholic alkali metal alkoxide solution through an inert fibrous material to give a first filtered solution, preferably with reduction of mercury to less than 5 ppm;

a second filtration step of filtering the first filtered solution using pulverized coal as a filtering aid, to give a second filtered solution preferably with further reduction of mercury to less than 0.5 ppm; and concentrating the second filtered solution by distillation to give a final product having less than 0.1 ppm mercury present.

It is surprising that an economical depletion of the mercury to contents of below 0.1 ppm, based on the solution, is only successful if the solution is first filtered through inert fibrous material, to remove the majority of the mercury and suspended matter, and an activated carbon treatment is not performed until afterward. It is equally surprising that the concentration step also contributes to the depletion of the mercury.

The alcoholic alkali metal alkoxide solutions used in method of the present invention are known in the art. Their preparation has been described in various of the references cited above and is known to those of skill in the art. These solutions include, but are not limited to alkali metal methoxide, ethoxide, propoxide, butoxide, etc., with the alcohol in which the alkali metal alkoxide is contained preferably being the alcohol from which the alkoxide moiety is derived (i.e. methoxide→methanol; ethoxide→ethanol; etc.).

For the first filtration, the prepurification, the inert fibrous material can be any alkali resistant fibrous material. It is preferably selected from polyethylene, polypropylene, polystyrene, mineral wool or cellulose. Preference is given to alkali-resistant fibrous materials made of mineral wool, with particular preference for mineral wool fibers processed to form beads or flakes. These can be readily introduced into the required filter vessels and can also be readily removed after use. In order to obtain a significant increase in service life, the prefiltration should produce a decrease in mercury and suspended solids which is achieved with the use of the described filter media. The abovementioned disadvantages of separators are thus avoided.

In the second filtration, a pulverized coal is used, preferably having an active surface area of 500 to 1500 $m^2/g$ and a particle size of 1 to 1000 $\mu m$, with products having an active surface area of 800 to 1200 $m^2/g$ and a particle size of 10 to 100 $\mu m$ being particularly preferred.

Surprisingly, it has been found that pulverized coal having a BET surface area of about 1000 $m^2/g$ and a fineness of grinding of 80% of the particles having a diameter of less than 40 $\mu m$ has a high efficiency of mercury removal in the treatment of alkali metal alkoxide solutions. Coal types having smaller specific surface areas or coarser particle sizes likewise produce a mercury depletion. However, higher remaining final concentrations of mercury must then be expected in these cases.

To treat the alkali metal alkoxide solutions, the fine pulverized coal is readily suspended in a first batch of the corresponding alkoxide solution for a period of time sufficient to permit interaction of the coal with mercury present in the solution, preferably from 0.1 to 60 min, more preferably from 0.1 to 10 min, most preferably from 0.1 to 5 min. The resulting slurry is then filtered through a disk filter. Using the coal layer formed by this means, further alkoxide solution can then be effectively freed from mercury in a continuous flow process. Pretreatments with metal salts or the like are not required, but can be used if desired.

The two filtration steps are advantageously carried out at temperatures which are between the crystallization point of the alkali metal alkoxide solution and 70° C. Preferably, filtration is performed at 15 to 35° C., more preferably from 20 to 30° C.

In the final step of concentrating the alkali metal alkoxide by distillation of the alcohol, the final depletion of mercury content to less than 0.1 ppm is achieved.

The filtrations are generally performed on 5 to 25% strength alkali metal alkoxide solutions. Solutions which have alkali metal alkoxide contents of preferably at least 20% are produced therefrom during the concentration, with final contents of 25 to 60% being particularly preferred. Alternatively, the alcohol can be completely distilled off at this point if desired.

The first filtration, through the inert material, leads to a marked removal of mercury from the alkali metal alkoxide solution. Thus, for example, a mercury content of 10 to 25 ppm is decreased to 1 to 2 ppm. At the same time, suspended matter and other contaminants are separated off. This provides effective protection of the fine coal layer in the second filtration, so that blockages can be avoided. The pulverized coal filtration decreases the mercury content once again to 1/5 to 1/10 its value prior to the coal filtration step. The final concentration step is frequently necessary in any case if a product having relatively high concentration is to be prepared. However, without the second filtration step, the concentration step does not effect a sufficient removal of mercury.

EXAMPLES

Having generally described this invention, a further understanding can be obtained by reference to certain specific examples which are provided herein for purposes of illustration only and are not intended to be limiting unless otherwise specified.

Examle 1

1000 g of pulverized coal having a specific surface area of 1000 $m^2/g$ and a fineness of grinding of 80% by weight of the particles having a diameter below 40 $\mu m$ were introduced into 300 l of a 20% strength methanolic sodium methoxide solution. A disk filter having a filter area of 0.7 m was precoated with this suspension. After formation of the coal layer, a 20% strength sodium methoxide solution having a photometrically measured turbidity of >20% at 25° C. was first passed through a vessel which contained 5 kg of beaded mineral wool for prefiltration, and was then passed through the prepared disk filter. The flow rate was approximately 200 l/h.

The sodium methoxide solution thus treated was then concentrated to approximately 30% in a distillation apparatus which was provided with a column packed with VA stainless steel packings. The Hg content of the sodium methoxide solution remaining in the still was determined.

| Feed | | After mineral wool | | After pulverized coal | | After concentration |
|---|---|---|---|---|---|---|
| Turbidity | Hg content | Turbidity | Hg content | Turbidity | Hg content | Hg content |
| >20% | 20 ppm | <1% | 1.5 ppm | <1% | 0.2 ppm | 0.03 ppm |

Example 2

2nd Stage 5 g of pulverized coal according to Example 1 were introduced into 100 ml of a 20% strength methanolic sodium methoxide solution. The resulting suspension was stirred at 70° C. for 4 hours and then filtered through a filter which retained all of the coal.

The Hg concentration decreased from 4 ppm to 0.028 ppm due to the coal treatment.

Example 3

2nd Stage

The procedure of Example 2 was followed, but use was made of a coal which had a specific surface area of 700 ml/g and a fineness of grinding of 99% by weight of particles having a diameter of above 44 $\mu m$.

In this case, the Hg concentration decreased from 4 ppm to 0.13 ppm.

Example 4

2nd Stage 10 g of pulverized coal according to Example 1 were introduced into 250 ml of a 20% strength sodium methoxide solution. The suspension thus obtained was placed in a G3 frit, having a diameter of 100 mm, which was connected via a rubber sleeve to a suction flask. A slight reduced pressure was established in the suction flask.

Before the alkoxide solution had completely passed through, new alkoxide solution was added at approximately 25° C. through the coal layer which formed. The flow rate was set to approximately 300 ml/in.

The Hg content was decreased by the coal treatment from 4.5 ppm to 0.22 ppm.

Example 5

2nd Stage

The procedure of Example 4 was followed, with the exception that 250 ml of a 20% strength sodium ethoxide solution were used instead of the sodium methoxide solution. A sodium ethoxide solution flowed through the coal layer which formed.

The Hg content was decreased by the coal treatment, from 4.8 ppm to 0.20 ppm.

Example 6

2nd stage

The procedure of Example 4 was followed, using 250 ml of a 20% strength potassium methoxide solution. The potassium methoxide solution flowed through the coal layer.

The Hg concentration decreased from 4.5 ppm to 0.25 ppm.

Example 7

2nd Stage

The procedure of Example 4 was followed using a potassium ethoxide solution.

The Hg concentration decreased in this case from 3 6 to 0.08 ppm.

Example 8

3rd Stage

The solution obtained from Example 4 was concentrated to a concentration of about 30% in a distillation apparatus provided with a column of 1 m in length that was packed with VA stainless steel spirals. The sodium methoxide solution remaining in the still after distillation had an Hg content of 0.05 ppm.

Comparison Example A

2nd Stage

A 20% strength sodium ethoxide solution having an Hg content of 28 ppm was directly subjected to a coal treatment as in Example 5, without performing the initial filtration through inert fibrous material.

The Hg content only decreased to 1.5 ppm.

Whereas the filtration through the coal layer in Example 1 could be performed for 6 weeks, until the mineral wool filter decomposed, without exhausting the coal layer, a service life of only approximately 8 days resulted with the coal layer of Comparison Example A.

This application is based on German priority Application 197 04 889.7, filed with the German Patent Office on Feb. 10, 1997, the entire contents of which are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A process for removing mercury-containing contaminants from an alcoholic alkali metal alkoxide solution, comprising:
    a first filtration step wherein the alcoholic alkali metal alkoxide solution is filtered through a non-silver coated inert fibrous material, to form a first filtered solution;
    a second filtration step wherein the first filtered solution is filtered using a pulverized coal as filter aid, to form a second filtered solution; and
    concentrating the second filtered solution by distillation.

2. The process as claimed in claim 1, wherein the inert fibrous material is an alkali-resistant fibrous material.

3. The process as claimed in claim 2, wherein the alkali-resistant fibrous material is a mineral wool.

4. The process as claimed in claim 3, wherein the mineral wool is selected from the group consisting of mineral wool flakes and mineral wool beads.

5. The process as claimed in claim 1, wherein the pulverized coal used in the second filtration step has an active surface area of 500 to 1500 $m^2/g$ and a particle size of 1 to 1000 $\mu$m.

6. The process as claimed in claim 5, wherein the pulverized coal has an active surface area of 800 to 1200 $m^2/g$ and a particle size of 10 to 100 $\mu$m.

7. The process as claimed in claim 1, wherein the second filtration step is performed using a disk filter having one or more disks coated with the pulverized coal.

8. The process as claimed in claim 1, wherein each of the first and second filtration steps is carried out at a temperature between the crystallization point of the alkali metal alkoxide solution and 70° C.

9. The process as claimed in claim 8, wherein the temperature for the first and second filtration steps is from 15 to 35° C.

10. The process as claimed in claim 9, wherein the temperature for the first and second filtration steps is from 20 to 30° C.

11. The process as claimed in claim 1, wherein in the distillation step, the second filtered solution is concentrated to give an alkali metal alkoxide content of at least 20% by weight of the solution.

12. The process as claimed in claim 1, wherein the first filtered solution has a mercury content of less than 5 ppm.

13. The process as claimed in claim 1, wherein the second filtered solution has a mercury content of less than 0.5 ppm.

14. The process as claimed in claim 13, wherein the resulting solution after the concentrating step has a mercury content of from $\frac{1}{5}$ to $\frac{1}{10}$ the mercury concentration of the second filtered solution.

15. The process as claimed in claim 1, wherein the resulting solution after the concentrating step has a mercury content of less than 0.1 ppm.

16. The process as claimed in claim 1, wherein, prior to the second filtration step, the first filtered solution is contacted with the pulverized coal for a period of time sufficient to provide interaction between the pulverized coal and mercury containing contaminants in the first filtered solution.

17. The process as claimed in claim 16, wherein said period of time is from 0.1 to 60 min.

18. The process as claimed in claim 17, wherein said period of time is from 0.1 to 10 min.

* * * * *